United States Patent

Plueddemann

[11] 3,956,353
[45] May 11, 1976

[54] ANIONIC COUPLING AGENTS

[75] Inventor: Edwin P. Plueddemann, Midland, Mich.

[73] Assignee: Dow Corning Corporation, Midland, Mich.

[22] Filed: July 15, 1974

[21] Appl. No.: 488,365

[52] U.S. Cl. .................... 260/448.8 R; 428/428; 428/420; 260/404; 260/404.5
[51] Int. Cl. ..................... C07f 7/10; C07f 7/18
[58] Field of Search ........... 260/448.8 R, 404, 404.5

[56] References Cited
UNITED STATES PATENTS

| | | | |
|---|---|---|---|
| 3,054,818 | 9/1962 | Pepe et al. ................... | 260/448.8 R |
| 3,171,851 | 3/1965 | Pepe ........................ | 260/448.8 R X |
| 3,317,577 | 5/1967 | Ryan ........................ | 260/448.8 R X |
| 3,624,120 | 11/1971 | Yetter ....................... | 260/448.8 R X |
| 3,819,675 | 6/1974 | Plueddemann ................ | 260/448.8 R |

*Primary Examiner*—Paul F. Shaver
*Attorney, Agent, or Firm*—Robert F. Fleming, Jr.

[57] ABSTRACT

Anionic silanes of the formula

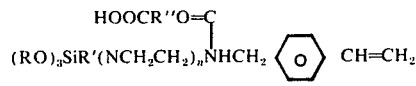

are made by reacting silanes of the formula

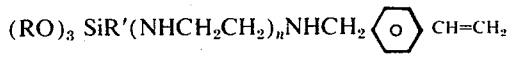

with 1 or 2 moles of an anhydride of a 1,2-dicarboxylic acid. A typical compound is

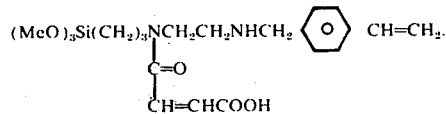

these compounds are used as coupling agents between inorganic substrates and organic resins such as epoxides, phenolic and polyester.

8 Claims, No Drawings

ANIONIC COUPLING AGENTS

One of the best types of general purpose coupling agents for fixing organic resins to inorganic substrates are the materials described and claimed in U.S. Pat. No. 3,819,675, the disclosure of which is incorporated herein in its entirety by reference. These silanes and the corresponding siloxanes are cationic materials and are amine or quaternary salts having the styryl group in the molecule. The latter is extremely reactive with practically all types of organic resin systems and because of the cationic nature of the molecule, it combines excellent wetting of a wide variety of substances with a high degree of reactivity with a wide variety of resins.

However, there is also need for an anionic silane which possesses the high degree of reactivity of the aforesaid cationic materials. Thus, the object of this invention is to provide coupling agents which give better wetting of acidic surfaces and which can be used in those rare instances in which the cationic materials are not satisfactory.

This invention relates to silanes of the formula

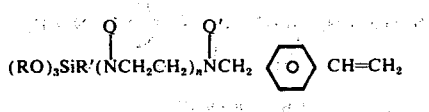

in which R is a lower alkyl or lower alkoxyalkyl radical, R' is an alkylene radical of 1 to 6 carbon atoms, Q and Q' are lower alkyl, hydrogen or the group

at least one Q or Q' being the latter group, the

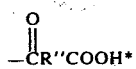

*Hereinafter called the acid-amide group.

group being derived from a 1,2-dicarboxylic anhydride**,

**Has the structure

R'' being divalent hydrocarbon, divalent chlorohydrocarbon or a divalent hydrocarbon radical containing one carboxyl group and $n$ is 0 or 1.

The compositions of this invention are prepared by reacting the amines of the aforesaid patent with 1,2-dicarboxylic acid anhydrides. In carrying out the reaction, it is best to employ the free amine rather than the amine salt. These free amines can be prepared by reacting the amine salts of the aforesaid patent with alkali metal alcoholates such as sodium methoxide. The reaction products of this invention are acid-functional amides and the reaction is carried out by mixing the anhydride with the amine in an appropriate solvent. When the reaction is carried out in polar solvents such as alcohols, the reaction is spontaneous and exothermic.

Where the starting amines contain 2 nitrogen atoms; i.e., where $n$ is 1, two moles of the anhydride can be reacted to give a product in which both Q and Q' are the amide-acid group. Also where two nitrogens are present in the amine and only 1 mol of anhydride is reacted, the resulting product is in effect, an amino acid and forms an internal zwitterion.

For the purpose of this invention, R can be any lower alkyl radical such as methyl, ethyl, isopropyl, butyl or hexyl, or any lower alkoxyalkyl radical such as beta-methoxyethoxy or beta-ethoxyethoxy. R' is an alkylene radical of 1 to 6 carbon atoms such as methylene, dimethylene, trimethylene, hexamethylene or 2-methylpropylene.

As can be seen, either Q or Q' can be hydrogen or a lower alkyl radical such as methyl, ethyl, propyl or butyl. Also, at least one Q or Q' must be the amide-acid group in which R'' can be any divalent hydrocarbon, any divalent chlorohydrocarbon, or any divalent hydrocarbon radical containing one carboxyl group. Since this group is derived from a 1,2-carboxylic anhydride, R'' must contain at least 2 carbon atoms. R'' can be saturated or unsaturated, it can be linear, branched or cyclic, aliphatic, cycloaliphatic, aromatic, aralkyl or alkaryl.

The various types of R'' groups are best illustrated by giving the anhydrides from which they are derived by reaction with the amines. Thus, the amide acid group can be derived from any of the following anhydrides. (For brevity, the term anhydride is omitted from each name.)

Where R'' is hydrocarbon, the anhydrides can be, for example, maleic, succinic, itaconic, citraconic, cyclohexene-4,5-dicarboxylic, 3,6-methylenecyclohexene-4,5-dicarboxylic, 3-methylbenzocyclohexane-1,2-dicarboxylic, 9,10-anthracyl succinic, propenyl succinic, dodecyl succinic, octadecyl succinic, dodecenyl succinic, phthalic, 3,2-naphthalene dicarboxylic, 1,2-naphthalene dicarboxylic, methyl phthalic and 3,4-dihydronaphthalene dicarboxylic. Where R'' is chlorinated, the anhydrides can be, for example, tetrachlorophthalic, chlorododecyl succinic, chloroanthracyl succinic or chlorododecenyl succinic. Where R'' contains a carboxyl group, the anhydride can be, for example, trimellitic, tricarballylic and aconitic.

When the compositions of this invention are exposed to moisture, they hydrolyze to the corresponding silanols and siloxanes and such hydrolyzates are the form of the material which is actually fixed to the inorganic substrate. The compositions of this invention are particularly useful as coupling agents and they can be applied to substrates either per se or in the form of organic solvent solutions, but preferably they are applied as an aqueous dispersion. The concentration of the silane applied to the substrate is not critical but normally from 0.1 to 1.0 percent aqueous dispersion is sufficient.

The compositions are useful on various kinds of inorganic substrates such as siliceous materials such as silica, glass, asbestos, clay, mica, talc or quartz and metal oxides, such as alumina and ferric oxide and metal substrates such as aluminum, magnesium, zinc, tin, chromium, titanium or steel. The amount of coupling agent on the surface of the substrate can vary from 0.01 to 10 percent or more by weight based on the weight of the substrate.

If desired, instead of pretreating the substrate, the compositions of this invention can be added to the organic resin. In this case the silane will migrate to the surface of the substrate when the resin is applied thereto. After the resin is brought into contact with the substrate, whether pretreated or treated in situ, the resin is cured thereby forming a composite article. The effectiveness of the coupling agents of this invention is shown by the increase in strength that is obtained under dry and wet conditions especially the latter.

The anionic materials are particularly effective with latex formulations of a wide variety of resins. The emulsifying agents in most latexes are anionic so the use of the instant coupling agents does not coagulate or otherwise adversely affect latexes. The silanes are added to the latex which is then applied to the substrate and dried.

The compositions of this invention are operative with organic resins, such as thermosetting resins such as unsaturated polyesters, butadiene-styrene resins, epoxy resins, phenolic resins, aminoplast resins, urethane resins or thermoplastic resins such as polyamides, polycarbonates, polyesters, and thermoplastic vinylic resins such as polyacrylates, polyvinyl chloride and polyvinyl acetate.

In addition to the above utility, those compounds of this invention containing long chain alkyl groups in R''*, can be used as emulsifying agents and such materials have a unique combination of properties in that they are both emulsifying agents and coupling agents. Thus, they can in effect be used as adhesive emulsifiers.

*For example, $C_{12}H_{25}\underset{\underset{CH_2-}{|}}{CH-}$

The compositions of this invention form salts when contacted with alkali metal hydroxides or aqueous ammonia or amines. In those cases where a free amine nitrogen is present, they can also form salts with acids. The preparation of the salts enhances the dispersibility of the compositions in aqueous media and such salts are considered to be within the scope of this invention. The solubility in aqueous medium is further enhanced when a carboxyl group is present in R''. These compositions can form salts at both carboxyl sites.

The following examples are illustrative only and should not be construed as limiting the invention which is properly delineated in the appended claims. In the examples, Me is methyl, Et is ethyl and Bu is butyl.

Example 1

To 75 parts by weight of a 50 percent methanol solution of the compound

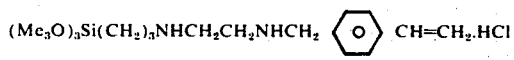

was added 50 g. of a 2 molal solution of sodium methoxide in methanol and there was an immediate formation of sodium chloride. The solution was filtered to obtain a methanol solution of the free amine.

PREPARATION OF COMPOUND I

A 1/10 mole solution of the above free amine in methanol was mixed with 10 g. of powdered maleic anhydride. An exothermic reaction took place to give a clear solution of the compound

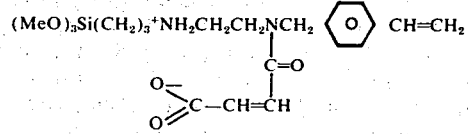

The structure of this compound was confirmed by infrared analysis.*

*The compound may contain some isomeric material in which the amide acid group is attached to the other N atom.

Example 2

PREPARATION OF COMPOUND II

To 0.1 mole of the free amine of Example 1 in methanol was added 20 g. of finely powdered maleic anhydride. An exothermic reaction took place to provide a clear solution of the compound

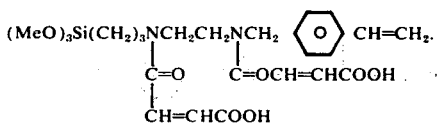

The structure of this compound was confirmed by infrared analysis.

Example 3

PREPARATION OF COMPOUND III

To a 0.1 mole solution of

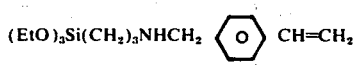

in methanol was added 10 g. of powdered maleic anhydride. The reaction was exothermic and gave a clear yellow solution of the compound

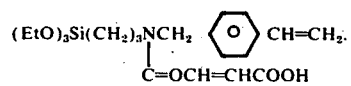

Example 4

PREPARATION OF COMPOUND IV

The experiment of Example 1 was repeated except that the anhydride used was succinic anhydride and the compound obtained was

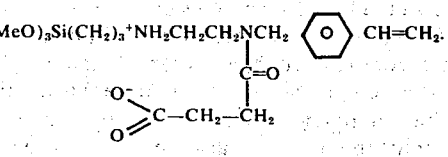

Example 5

PREPARATION OF COMPOUND V coupling agents is shown by the excellent retention of strength under wet conditions.

| Compound | pH of Aqueous Solution | Flexural Strength of Composite (p.s.i. × 10⁻³) | | |
|---|---|---|---|---|
| | | Dry | 2 Hr. H₂O Boil | 72 Hr. H₂O Boil |
| I | 4 | 71.4 | 67.3 | 40.9 |
| | 6 | 75.2 | 80.3 | 48.6 |
| | 8 | 79.7 | 81.6 | 48.3 |
| | 10 | 77.9 | 78.4 | 41.6 |
| II | 4 | 88.4 | 82.5 | 46.9 |
| | 6 | 78.4 | 80.5 | 41.9 |
| | 8 | 79.9 | 72.7 | 31.7 |
| | 10 | 82.9 | 80.1 | 37.3 |
| III | 4 | 82.1 | 80.5 | 41.3 |
| | 6 | 79.8 | 78.5 | 44.7 |
| | 8 | 83.7 | 82.0 | 43.4 |
| | 10 | 77.2 | 66.0 | 27.5 |
| Blank | — | 56.1 | 34.8 | — |

The experiment of Example 3 was repeated except that the anhydride used was succinic anhydride and the compound obtained was

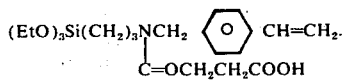

Example 6

Following the procedure of Example 1, the free amine of that example was reacted with an equal molar amount of the anhydrides shown below in methanol. In each case the monoamide carboxylic acid product was obtained, i.e.

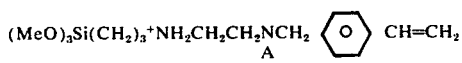

where A is the amide acid group. The anhydrides employed were phthalic anhydride, cyclohexanedicarboxylic-1,2-anhydride, 5-methyl-3,6-(methano)-cyclohexane-1,2-dicarboxylic anhydride, dodecenyl succinic anhydride and decenyl succinic anhydride. The run with dodecenyl succinic anhydride was repeated using two mols of the anhydride and the product having two acid-amide groups was obtained.

Each of the above products was dispersed in water and applied to glass slides and allowed to dry. Polyester resin was then molded against the treated glass slide and in each case the adhesion of the polyester resin to the glass slide was better than to a glass slide which was untreated.

Example 7

Each of the compounds shown below were applied to E Glass Cloth, style 7781 by immersing the cloth in a 0.25 percent by weight aqueous dispersion of the compound, said dispersion having the pH's shown below. The pH was adjusted using acetic acid or ammonia. The cloth was then air dried and heated 7 minutes at 230°F. The treated glass cloth was then formed into a 12 ply laminate with Paraplex P-43 polyester resin and cured. The cured laminates were 33 percent resin and 67 percent glass. The flexural strength of each of the laminates was determined dry, after a two hour boil and after a 72 hour boil in water. The results are shown in the table below and the effectiveness of the materials as

Example 8

The compounds shown below were applied to glass microspheres in the form of a 0.25 percent by weight aqueous solution having a pH of 9. The treated spheres were then dried and incorporated in a polyester resin Paraplex P-43 in amount of 150 parts glass microspheres per 100 parts of resin. The resin was cured and the flexural strength of the casting in p.s.i. was determined dry and after a two hour water boil. The results are shown in the table below:

| Compound | Flexural Strength of Casting (p.s.i.) | |
|---|---|---|
| | Dry | 2 Hr. H₂O Boil |
| Blank | 9,300 | 5,400 |
| I | 17,700 | 12,700 |
| II | 15,000 | 8,100 |
| III | 16,900 | 10,700 |
| IV | 16,700 | 10,300 |
| V | 17,300 | 11,400 |

Example 9

Compound I was applied to Pennsylvania Glass Sand of 5 micron particle size by slurrying the sand with an aqueous dispersion of the compound at a pH of 5.5. The slurry was dried and the resulting sand had a pickup of 1 percent by weight organosilicon compound. The sand was mixed with polyester resin Paraplex P-43 in amount of 150 parts sand per 100 parts of resin. The resin was cured and the casting was found to have a flexural strength of 15,600 p.s.i. dry and 10,400 p.s.i. after a 2 hour boil in water. Untreated sand gave an initial strength of 9,500 p.s.i. and 6,500 p.s.i. after a 2 hour water boil.

Example 10

The compounds I and II were applied to E-Glass Cloth style 7781 from an aqueous dispersion in amount of 0.25 percent by weight hydrolyzate at a pH of 8. The cloth was then air dried and heated at 230°F. for 7 minutes. The cloth was formed into a 14 ply laminate with bis-phenol-A epoxy resin cured with metaphenylene diamine. The flexural strength of the composite was determined according to the table below:

| Compound | Flexural Strength of Composite (p.s.i. × 10⁻³) | | |
|---|---|---|---|
| | Dry | 2 Hr. H₂O Boil | 72 Hr. H₂O Boil |
| I | 84.7 | 79.9 | 66.3 |
| II | 93.3 | 81.3 | 70.8 |

-continued

| Compound | Flexural Strength of Composite (p.s.i. × 10⁻³) | | |
|---|---|---|---|
| | Dry | 2 Hr. H₂O Boil | 72 Hr. H₂O Boil |
| Blank | 69.1 | 64.2 | 30.5 |

Example 11

When one mol of maleic anhydride is reacted with the following amines in accordance with the procedure of Example 1, the following amides are obtained. A is the $$-\overset{O}{\underset{\|}{C}}-CH=CHCOOH \text{ group.}$$

| Amine | Amide |
|---|---|
| (MeO)₃SiCH₂NHCH₂⟨O⟩CH=CH₂ | (MeO)₃SiCH₂NCH₂⟨O⟩CH=CH₂ <br> A |
| (BuO)₃Si(CH₂)₂NHCH₂⟨O⟩CH=CH₂ | (BuO)₃Si(CH₂)₂NCH₂⟨O⟩CH=CH₂ <br> A |
| (MeOCH₂CH₂O)₃Si(CH₂)₃N(CH₃)CH₂CH₂NHCH₂⟨O⟩CH=CH₂ | (MeOCH₂CH₂O)₃Si(CH₂)₃N(CH₃)CH₂CH₂NCH₂⟨O⟩CH=CH₂ <br> A |
| Me  Bu <br> (MeO)₃SiCH₂ĊHCH₂ṄCH₂CH₂NHCH₂⟨O⟩CH=CH₂ | Me  Bu <br> (MeO)₃SiCH₂ĊHCH₂ṄCH₂CH₂NCH₂⟨O⟩CH=CH₂ <br> A |

Example 12

When the amine of Example 3 is reacted with the following anhydrides, the following products are obtained.

| Anhydride | Product |
|---|---|
| chlorododecyl succinic | (EtO)₃Si(CH₂)₃NCH₂⟨O⟩CH=CH₂ <br> C=O <br> ĊHCH₂COOH <br> C₁₂H₂₄Cl |
| 3-methyl-benzo-cyclohexane-1,2-carboxylic | 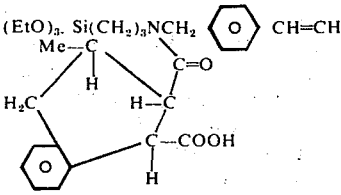 |
| tetrahydrophthalic | (EtO)₃Si(CH₂)₃NCH₂⟨O⟩CH=CH₂ <br> C=O <br> ⟨COOH⟩ |
| tetrachlorophthalic | (EtO)₃Si(CH₂)₃NCH₂⟨O⟩CH=CH₂ <br> C=O <br> Cl₂⟨COOH⟩Cl₂ |

-continued

| Anhydride | Product |
|---|---|
| trimellitic | (EtO)₃Si(CH₂)₃NCH₂⟨O⟩CH=CH₂ <br> C=O <br> ⟨O⟩COOH <br> COOH |
| octadecyl succinic | (EtO)₃Si(CH₂)₃NCH₂⟨O⟩CH=CH₂ <br> C=O <br> C₁₈H₃₇—ĊHCHCOOH |
| 1,2,3,3,6,6-hexa-chlorocyclo-hexene-4,5-di-carboxylic | (EtO)₃Si(CH₂)₃NCH₂⟨O⟩CH=CH₂ <br> C=O <br> Cl₂⟨COOH⟩Cl₂ <br> Cl |

That which is claimed is:

1. A composition of matter of the formula $$(RO)_3SiR'(\overset{Q}{N}CH_2CH_2)_n\overset{Q'}{N}CH_2 \langle O \rangle CH=CH_2$$

in which
R is a lower alkyl or lower alkoxyalkyl radical,
R' is an alkylene radical of 1 to 6 carbon atoms,
Q and Q' are lower alkyl, hydrogen or the group $$-\overset{O}{\underset{\|}{C}}R''COOH,$$

at least one Q or Q' being the latter group, the $-\overset{O}{\underset{\|}{C}}R''COOH$ group being derived from a 1,2-dicarboxylic anhydride, R" being divalent hydrocarbon, divalent chlorohydrocarbon or a divalent hydrocarbon radical containing one carboxyl group and $n$ is 0 or 1.

2. An aqueous dispersion of the composition of claim 1.

3. An aqueous dispersion of an alkali metal amine or ammonium salt of the composition of claim 1.

4. A composition of claim 1 of the formula

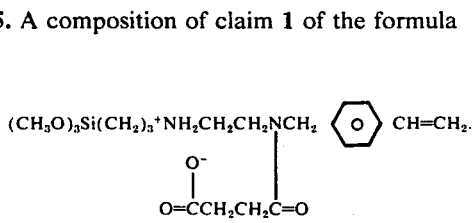

5. A composition of claim 1 of the formula

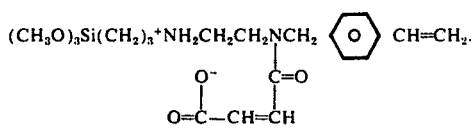

6. A composition of claim 1 of the formula

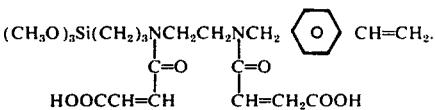

7. A compound of claim 1 of the formula

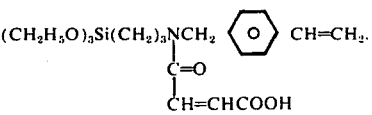

8. A compound of claim 1 of the formula

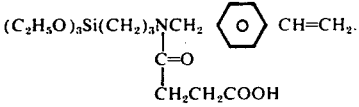

* * * * *

UNITED STATES PATENT OFFICE
CERTIFICATE OF CORRECTION

Patent No. 3,956,353    Dated May 11, 1976

Inventor(s) Edwin P. Plueddemann

It is certified that error appears in the above-identified patent and that said Letters Patent are hereby corrected as shown below:

Column 10, line 14, portion of the formula "$(CH_2H_5O)_3$" should read --$(C_2H_5O)_3$--.

Signed and Sealed this

Twenty-first Day of December 1976

[SEAL]

Attest:

RUTH C. MASON
*Attesting Officer*

C. MARSHALL DANN
*Commissioner of Patents and Trademarks*